(12) United States Patent
Yajima et al.

(10) Patent No.: US 7,323,442 B2
(45) Date of Patent: Jan. 29, 2008

(54) AGENTS FOR ALLEVIATING SYMPTOMS ACCOMPANIED BY INFLAMMATION

(75) Inventors: Masako Yajima, Tokyo (JP); Makiko Nakayama, Ibaraki-Ken (JP); Yumi Tsukamoto, Tokyo (JP); Kaoru Koide, Tokyo (JP); Tamotsu Kuwata, Saitama-ken (JP); Takaji Yajima, Tokyo (JP)

(73) Assignee: Meiji Dairies Corporation, Tokyo (JP)

( * ) Notice: Subject to any disclaimer, the term of this patent is extended or adjusted under 35 U.S.C. 154(b) by 271 days.

(21) Appl. No.: 10/073,297

(22) Filed: Feb. 13, 2002

(65) Prior Publication Data
US 2002/0111295 A1 Aug. 15, 2002

(30) Foreign Application Priority Data
Feb. 15, 2001 (JP) .............................. 2001-038486

(51) Int. Cl.
*A61K 38/16* (2006.01)
*A61K 35/14* (2006.01)
(52) U.S. Cl. .................... 514/6; 530/382; 530/383; 530/385
(58) Field of Classification Search .................... 514/6; 530/362, 363, 365
See application file for complete search history.

(56) References Cited

U.S. PATENT DOCUMENTS 5,240,909 A * 8/1993 Nitsche .......................... 514/8
2006/0039921 A1 * 2/2006 MacDonald et al. ...... 424/190.1

FOREIGN PATENT DOCUMENTS

| EP | 0 584 558 | | 3/1994 |
| JP | 8-165248 | * | 6/1996 |
| JP | 10-114675 | | 5/1998 |

OTHER PUBLICATIONS

Elass-Rochard et al., Infection and Immunity, vol. 66, No. 2, pp. 486-491, Feb. 1998.*
Martins et al., Clinical and Diagnostic Laboratory Immunology, vol. 2, No. 6, pp. 763-765, Nov. 1995.*
Patent Abstracts of Japan, JP 51-78759, Jul. 20, 1993.
Patent Abstracts of Europe, EP 0 579 830, Jan. 26, 1994.
Patent Abstracts of Japan, JP 7-300425, Nov. 14, 1995.
Patent Abstracts of Japan, JP 10-114675, May 6, 1998.
Patent Abstracts of Japan, JP 10-245347, Sep. 14, 1998.
Patent Abstracts of Japan, JP 11-029600, Feb. 2, 1999.
Patent Abstracts of Japan, JP 2000-229881, Aug. 22, 2000.
E. Elass-Rochard, et al., Infection and Immunity, vol. 66, No. 2, pp. 486-491, "Lactoferrin Inhibits the Endotoxin Interaction With CD14 by Competition With the Lipopolysaccharide-Binding Protein", Feb. 1998.
D. Jean, et al., American Journal of Respiratory and Critical Care Medicine, vol. 158, pp. 1702-1708, "Protective Effect of Endotoxin Instillation on Subsequent Bacteria-Induced Acute Lung Injury in Rats", 1998.
M. Machnicki, et al., Int. J. Exp. Path., vol. 74, pp. 433-439, "Lactoferrin Regulates the Release of Tumour Necrosis Factor Alpha and Interleukin 6 in Vivo", 1993.
O. Levy, Antimicrobial Agents and Chemotherapy, vol. 44, No. 11, pp. 2925-2931, "A Neutrophil-Derived Anti-Infective Molecule: Bactericidal/Permeability-Increasing Protein", Nov. 2000.
M. Yajima, et al., FASEB Journal, vol. 13, No. 4, A591 (1999).
M. Yajima, et al., The 4th International Conference on Lactoferrin, Program & Abstract, pp. 77 (1999).
5th International Conference on Lactoferrin: Structure, Function and Applications, May 4-9, 2001, Banff, Alberta Canada.

* cited by examiner

*Primary Examiner*—Jon Weber
*Assistant Examiner*—Abdel A Mohamed
(74) *Attorney, Agent, or Firm*—Oblon, Spivak, McClelland, Maier & Neustadt, P.C.

(57) ABSTRACT

The present invention provides agents for alleviating symptoms resulting from inflammation, which have an activity to alleviate inflammatory symptoms caused by bacterial infection, particularly accumulation of body fluid such as bronchocavemous plasma exudation, ascites, etc., at the inflammatory site, or excessive increase of blood neutrophils; symptoms resulting from inflammation caused by bacterial infection, particularly accumulation of body fluid such as bronchocavemous plasma exudation ascites, etc., at the inflammatory site, or excessive increase of blood neutrophils, can be alleviated effectively by ingesting or administering orally or parenterally a composition containing human-type lactoferrin as an effective component.

18 Claims, 7 Drawing Sheets

FIG. 1

Effect of prophylactic administration of human-type lactoferrin on accumulation of albumin by intraperitoneal administration of LPS

FIG. 2

Study of influence of LPS on the blood neutrophil number and the effect of human-type lactoferrin on the suppression of excessive increase of neutrophil number

FIG. 3

Comparison of the effect of human-type lactoferrin(hLF) and bovine-type lactoferrin(bLF) on the albumin concentration in lavage-fluid of the abdominal cavity detected under LPS induction; hLF: SIGMA Chemical Co. ; bLF:Wako Pure Chemical Ind.

FIG. 4

The effect of human-type lactoferrin(hLF) and bovine-type lactoferrin (bLF) on the TNFα concentration in the plasma detected under LPS induction hLF:SIGMA Chemical Co.;  bLF:Wako Pure Chemical Ind.

FIG. 5

Effect of human-type lactoferrin on accumulation of ascites under LPS-induced inflammation
    hLF:SIGMA Chemical Co.

FIG. 6

Effect of human-type lactoferrin on albumin accumulation in the abdominal cavity under LPS induction: Difference in the time of lactoferrin administration
( − before administration time   + after administration time )

FIG. 7

AGENTS FOR ALLEVIATING SYMPTOMS ACCOMPANIED BY INFLAMMATION

FIELD OF THE INVENTION

The present invention relates to agents for alleviating symptoms resulting from inflammation, which are effective for alleviating inflammatory symptoms caused by lipopolysaccharides that are brought about by bacterial infection, etc., particularly symptoms such as accumulation of body fluid such as bronchocavemous plasma exudation, ascites, etc., at the inflammatory site, or excessive increase of blood neutrophils.

PRIOR ART

Human or mammalian milk contains antimicrobial materials such as immunoglobulins, e.g., secretory IgA or IgG, complements, lysozyme, lactoferrin, etc. It is known that ingestion of mother's milk decreases the incidence of infectious diseases or the incidence period, compared to that of artificial milk which contains almost no antimicrobial materials.

Among these antimicrobial materials, it has been demonstrated in vitro that lactoferrin forms a chelate with iron to mainly inhibit growth of *Escherichia coli*, etc., and shows a bactericidal effect. Moreover, in addition to such a bactericidal effect, a variety of pharmacological effects have already been reported. For example, Japanese Patent Laid-Open No. 178759/1993 discloses an immune activation effect, Japanese Patent Laid-Open No. 2000-229881 discloses an effect of prognostic improvement, Japanese Patent Laid-Open No. 300425/1995 discloses an effect of inhibiting adhesion of pathogenic bacteria to the target cells, Japanese Patent No. 2840795 discloses an effect of promoting growth of cells, and so on.

On the other hand, in inflammatory diseases, for example, ascites in peritonitis and bronchocavemous plasma exudation in pneumonitis are retained respectively to cause a decrease of physical strength of patients. Also, severe exudation of neutrophils and tissue damage are induced in the inflammatory site. In sepsis caused by gram-negative bacilli, it is known that decline in blood albumin concentration, decrease of lymphocytic leukocytes, and increase of neutrophils occur and sometimes induce deterioration of the symptom, which in turn is developed into a systemic inflammatory reactive syndrome such as multiple organ failure, for which the prognosis is quite worse. In order to improve these symptoms resulting from inflammation, it has been attempted to administer a human-type albumin preparation into blood, but no sufficient alleviation effect for the symptoms has been recognized. In a case of serious invasion such as injury or a highly inflammatory state such as severe infection, it is considered that a large quantity of plasma water, would exude into the tissue because of asthenia of the endothelial permeability. In such a case, it has been reported that the use of a colloidal material such as an albumin preparation to alleviate the symptom has unexpectedly increased the risk of death. There is accordingly a demand for the development of a new agent to effectively alleviate these symptoms.

In this situation, there are some reports that a soybean Kunitz-type trypsin inhibitor disclosed in Japanese Patent—Publication No. 121869/1995 and a vascular endothelial cell growth factor/vasopermeable factor antagonist disclosed in Japanese Patent Laid-Open No. 245347/1998 have an effect of suppressing accumulation of body fluid to prevent decline of the physical strength of patients and to enhance therapeutic effect. In the case of lactoferrin as mentioned above, an example in which a peptide derived from lactoferrin is used as an agent for suppressing inflammation caused by an endotoxin (lipopolysaccharide (LPS)) derived from gram-negative bacteria is disclosed in Japanese Patent Laid-Open No. 165248/1996. Another example in which lactoferrin per se is used in combination in treatment for diseases induced by the endotoxin is disclosed in Japanese Patent Laid-Open No. 114675/1998. It has never been examined, however, whether lactoferrin can be used to alleviate the exudation of plasma albumin at the inflammatory site or the increase of blood neutrophils.

PROBLEMS THAT THE INVENTION IS TO SOLVE

In this situation, the present inventors worked assiduously to study the effect of lactoferrin on various symptoms caused by inflammation, and they found first that, in addition to the various pharmacological effects reported so far, lactoferrin showed an effect alleviating various symptoms which appeared after infection. They further studied such an effect to compare human-type lactoferrin with bovine-type lactoferrin which has usually been used. Contrary to their expectation, they first found that particularly the human-type lactoferrin showed a potent effect alleviating the symptoms. The invention was completed based on these findings. Thus, the invention provides novel agents for alleviating or improving various symptoms or a pathologic state caused by a complication resulting from inflammation such as sepsis developing as sequelae in post-operative patients or burned patients or long-term inpatients.

MEANS FOR SOLVING THE PROBLEMS

The present invention relates to agents for alleviating symptoms caused by inflammation comprising human-type lactoferrin as an effective ingredient, which are characterized by suppression of exudation of albumin or body fluid to the inflammatory site or of increase of blood neutrophils. The human-type lactoferrin used in the invention may be a commercially available one or one obtained from human mother's milk in a known method (e.g., Japanese Patent Laid-open No. 29600/1999). When a large quantity is used, a recombinant human-type lactoferrin made in some other species of cells by a gene manipulation technique disclosed in Japanese Patent No. 2824332 may be utilized.

The main ingredient in the agent for alleviating symptoms resulting from inflammation according to the invention primarily exists in human milk, which is superior in safety and considered to have no strong antigenicity to human as bovine-derived proteins. Thus, it may be used preferably in a subject such as neonates or infants. It may be administered parenterally, for example, intravenously, intramucosally, percutaneously, intraperitoneally, etc., or orally with no problem. Preferably, parenteral administration is employed because the dose can be reduced. Moreover, in addition to human, pet animals such as dog, cat, etc., or livestock such as bovine, swine, equine, sheep, etc. may be used as the subject to be administered. In oral administration, conventional tablets, powders, syrup, formulated powdered milk, etc. may be employed, or it may be used as an additive to foods or drinks. In parenteral administration, it may be administered as an aqueous solution for injection, transfusion, washes of wound parts, or enteral nutritives. Alternatively, it may be used as a wash through a tube for enteral nutrition attached to a patient.

These preparations may be prepared in the same known method as for bovine-type lactoferrin. For example, a method for preparing a preparation for oral administration such as tablets, syrup, capsules, etc. is described in Japanese Patent Laid-Open No: 2000-229881. The aqueous preparation for injection can be prepared according to the method as disclosed in Japanese Patent Laid-Open No. 48956/1994, etc.

The product of the invention was evaluated by confirming the in vivo effect in an animal experiment using rats. As a result, it was confirmed that administration of human-type lactoferrin reduced both accumulation of albumin that was exuded in the abdominal cavity and decline of blood albumin concentration caused by inductivity of LPS administered in the abdominal cavity, and greatly suppressed the symptoms such as increase of neutrophils caused by inflammation. In the invention, a variety of pharmaceutical formulations containing human-type lactoferrin may be administered to a patient or immune insufficient subject to whom an inflammatory disease such as sequela sepsis is possibly expected to develop. Thus, it has become first possible to utilize an agent containing human-type lactoferrin as an effective ingredient in order to suppress exudation of albumin at the inflammatory region or decrease blood albumin concentration, hasten recovery of a usual level of blood neutrophils, and suppress increase of neutrophils.

The effective dose of human-type lactoferrin for parenteral administration in the invention is 0.1 mg-20 mg/kg/day for intravenous injection, desirably 0.5 mg-10 mg/kg/day, and 1 mg-200 mg/kg/day for intraperitoneal administration. In oral administration, 5 mg/kg/day to 1000 mg/kg/day, preferably 20 mg/kg/day to 1000 mg/kg/day is used.

EXAMPLES

The following examples serve to specifically illustrate the invention, but the invention is not limited to these examples.

Example 1

Study of the Effect of Human-Type Lactoferrin on Alleviation of Symptoms Resulting from LPS-Induced Inflammation (Accumulation of Albumin in the Abdominal Cavity and Increase of Blood Neutrophils)

Test method: Human-type lactoferrin used in the test was the product of SIGMA Chemical Co. Rat pups of 13 days of age (Sprague-Dawley rat; Japan SLC, Inc.) were assigned to 3 groups in random order to eliminate the influence of inter litter variation, each group consisting of 8 rats. 5% Casein solution was administered to all groups in order to provide uniform proteinous stimulation to the rats. Specifically, to two groups involving a control group were given 100 microliters of 5% casein solution and 100 microliters of phosphate-buffered physiological saline, and to the remaining group were given 100 microliters of 5% casein solution and 100 microliters of 10% human-type lactoferrin solution. After 18 hours, LPS (Difco: B, *E. coli* 055:B5) derived from *Escherichia coli* was administered intraperitoneally in an amount of 0.2 micrograms per gram of the body weight. To the control group, an equal amount of phosphate-buffered physiological saline was administered instead of the LPS. Five hours or 24 hours after administration of LPS, the rat pups were anesthetized with ether, and 1 ml of chilled phosphate-buffered physiological saline was intraperitoneally injected and massaged well to collect lavage-fluid from the abdominal cavity. Then, the blood was collected from the abdominal aortas. The lavage-fluid from the abdominal cavity was centrifuged at 300×g for 5 minutes, and the resulting supernatant was preserved at −80° C. as a sample for measurement of proteins. The total protein concentration in the lavage-fluid from the abdominal cavity was determined by means of Coomassie Blue, and albumin was determined using a kit purchased from Wako Pure Chemical Industries Ltd. A part of the blood was collected with a blood-collecting tube containing dipotassium ethylenediaminetetra-acetate (EDTA) and outside blood-testing facility was employed to analyze blood cell features. The remaining part was allowed to stand at room temperature for 30 minutes, then cooled, and centrifuged to give a plasma fraction, which was preserved at −80° C. until use. A part of the plasma was used for determination of the content of tumor necrosis factor alpha (TNFα) using a sandwich ELISA kit for rats commercially available, and another part for determination of the albumin concentration using a kit from Wako Pure Chemical Ind.

Figure 1:
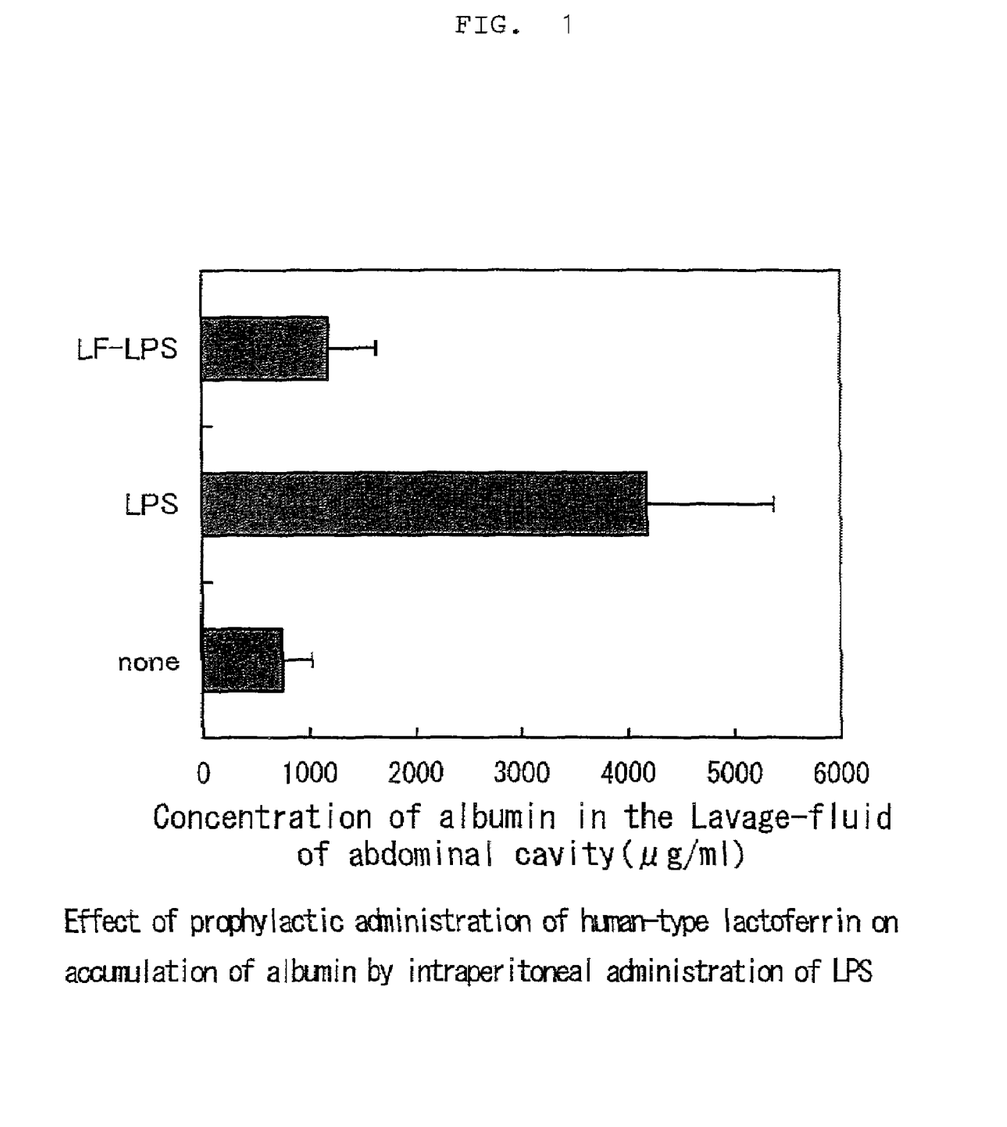
FIG. 1 shows an effect of human-type lactoferrin on reducing the concentration of albumin contained in the lavage-fluid of an abdominal cavity 5 hours after administration of lipopolysaccharide (LPS).
Figure 2:
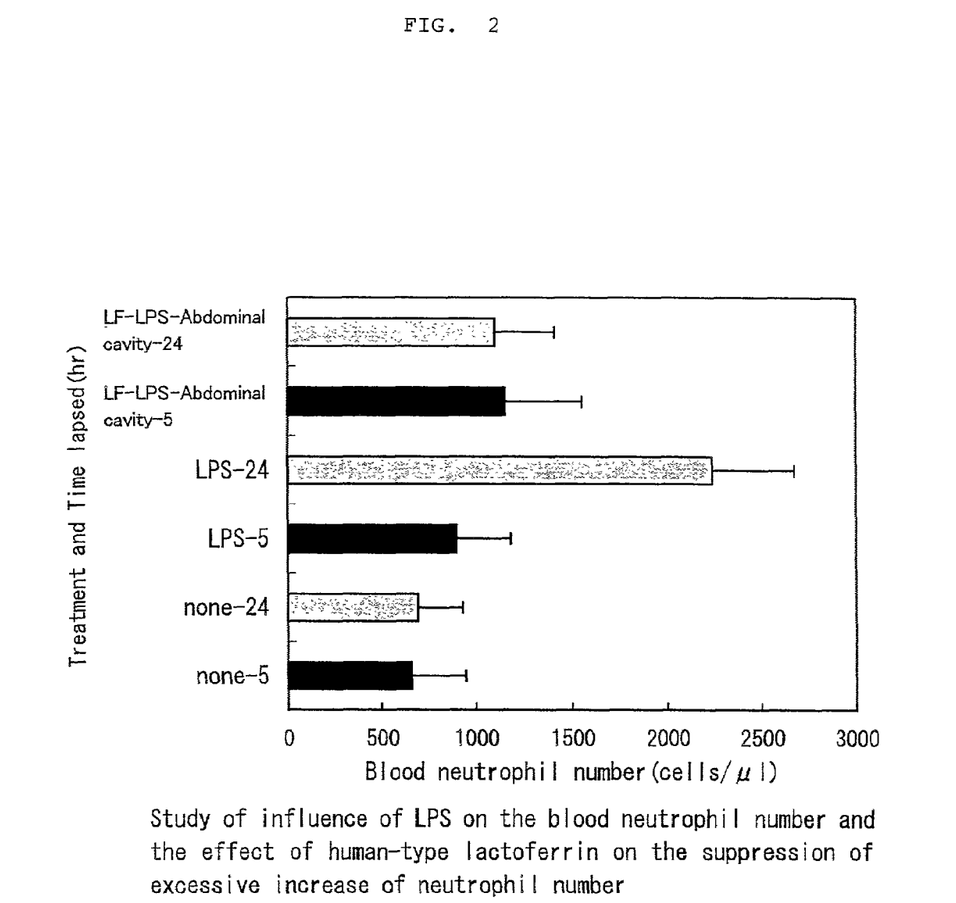
FIG. 2 shows an effect of human-type lactoferrin on inhibiting increase of the number of blood neutrophils 5 hours and 24 hours after administration of LPS.

Test Results: FIGS. 1 and 2 show the results of the test. FIG. 1 shows a reducing effect of human-type lactoferrin on accumulation of albumin in the lavage-fluid of abdominal cavity 5 hours after administration of LPS. The vertical axis indicates test groups and the horizontal axis indicates the albumin concentration in the lavage-fluid of the abdominal cavity. As apparent from FIG. 1, exudation and accumulation of albumin at the inflammatory region (the abdominal cavity in this case) induced by administration of LPS was markedly suppressed in the group to which human-type lactoferrin was previously administered, compared to the group to which no lactoferrin was administered. FIG. 2 shows the number of blood neutrophils 5 hours and 24 hours after administration of LPS. Five hours after administration of LPS, the number of neutrophils was slightly decreased, and that of lymphocytes was significantly decreased. Twenty-four hours after administration of LPS, the number of lymphocytes was almost recovered. As shown in FIG. 2, the numbers of the blood-neutrophils increased more excessively after administration of LPS in the group without preliminary administration of human-type lactoferrin (hLF) than the counterparts in the group with hLF. The number of the blood neutrophils in the group with preliminary administration of hLF was at a similar level to that in the group without administration of both hLF and LPS. By the preliminary administration of hLF, LPS-induced inflammation was alleviated and excessive increase of blood neutrophils was prevented.

Example 2

Comparison of the Effect of Human-Type Lactoferrin with that of Bovine-Type Lactoferrin on Alleviation of Symptoms (Accumulation of Albumin in the Abdominal Cavity) Resulting from Inflammation Induced by LPS Test Method: The human-type lactoferrin used in the test was purchased from SIGMA Chemical Co., and the bovine-type lactoferrin was the product of Wako Pure Chemical Ind. The test was carried out in the same manner as in Example 1. The human-type and bovine-type lactoferrins each was dissolved in a phosphate-buffered physiological saline free of LPS at a concentration of 10%, and used after sterile filtration. Rat pups of 13 days of age (Sprague-Dawley rat; Japan SLC, Inc.) were assigned in random order to eliminate the influence of inter litter variation into 6 groups, each group consisting of 5 rats. To all groups was administered 5% casein solution in order to provide uniform proteinous stimulation to the rats. Specifically, to two groups involving a control group were intraperitoneally given 100 microliters of 5% casein solution and 100 microliters of phosphate-buffered physiological saline, and to the 2 groups of the remaining 4 groups were given 100 microliters of 5% casein solution and 100 microliters of 10% human-type lactoferrin solution. And, to the remaining 2 groups were intraperitoneally given 100 microliters of 5% casein solution and 100 microliters of 10% bovine-type lactoferrin solution, respectively. Eighteen hours after the administration, 0.2 microgram/g of body weight of LPS derived from *Escherichia coli* was intraperitoneally administered to one of two groups to which the same materials were given, and the same volume of phosphate-buffered physiological saline was given to the other (of two groups). Five hours after administration of LPS, the lavage-fluid of the abdominal cavity was collected under anesthetization with ether in the same manner as Example 1. The total protein concentration and the concentration of albumin contained in the lavage-fluid from the abdominal cavity were determined. The concentration of TNFα in the plasma was determined with a sandwich ELISA kit for rats.

Figure 3:
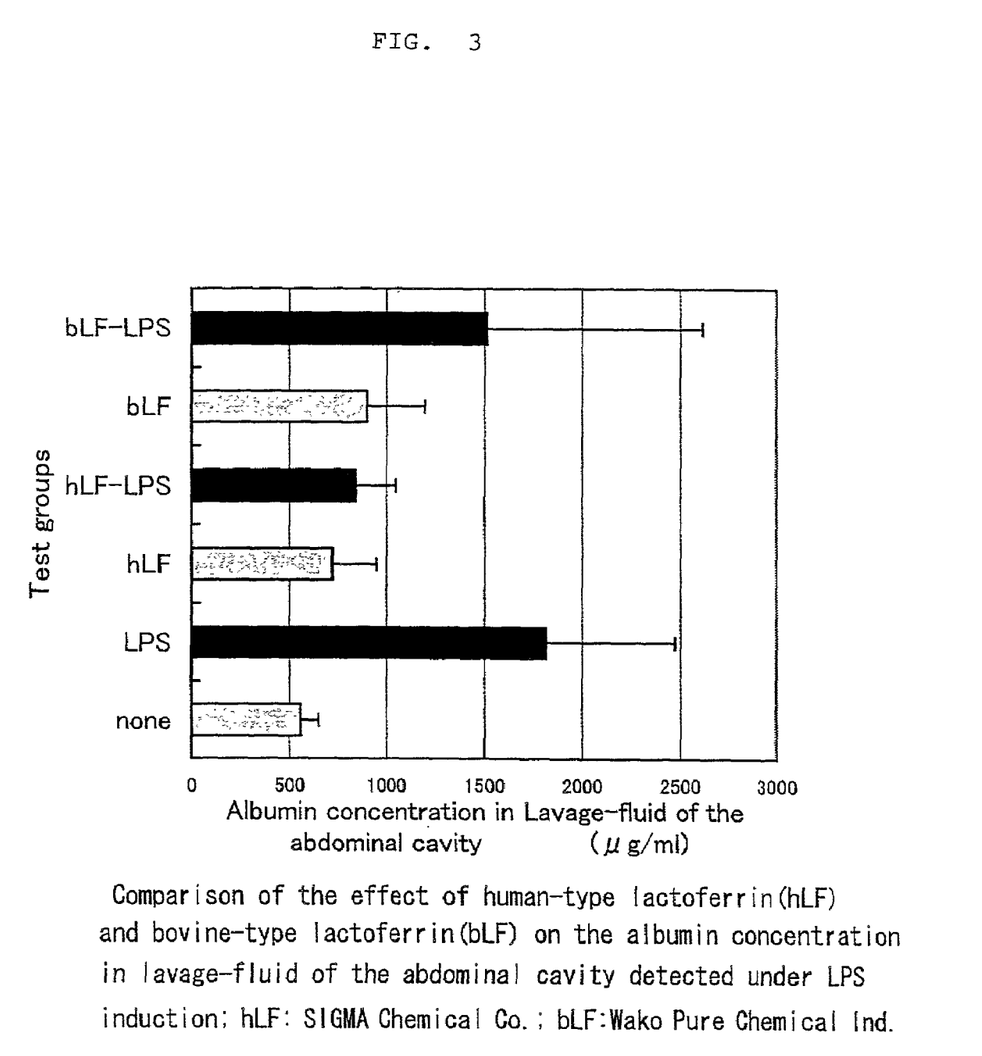
FIG. 3 shows an improved effect of human-type or bovine-type lactoferrin on exudation of albumin in the abdominal cavity in the inflammation induced by LPS.
Figure 4:
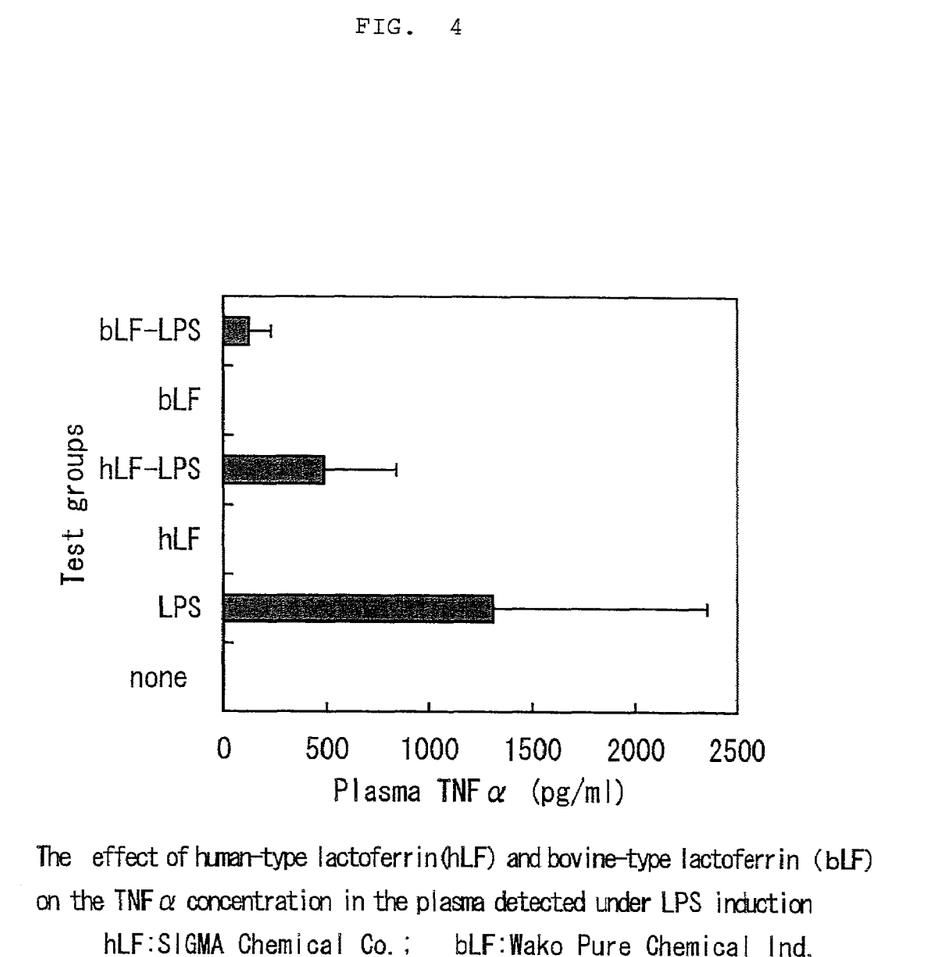
FIG. 4 shows comparatively an inhibitory effect of human-type or bovine-type lactoferrin on the plasma TNFα production in the inflammation induced by LPS.

Test Result: As seen from the result as shown in FIG. 3, the albumin concentration in the lavage-fluid of abdominal cavity in the group to which human-type lactoferrin was administered, even though LPS was administered, was approximately the same as that of the control group to which no LPS was administered, indicating no albumin accumulation. On the other hand, in the group to which bovine-type lactoferrin was administered, accumulation of albumin was observed after administration of LPS, in which the accumulation level of exuded albumin was as high as in the group to which lactoferrin was not administered but LPS was administered. The result was the same as in the experimentation which was carried out in the same manner as above using bovine-type lactoferrin purchased from SIGMA Chemical Co. These results indicate that the local exudation and accumulation of albumin caused by LPS-induced inflammation can be prevented by administration of human-type lactoferrin in advance, but the effect cannot be expected with bovine-type lactoferrin. In the 2 groups to which lactoferrin was administered but no LPS was administered, the concentration of protein and albumin in the abdominal cavity was as low as in the control group. As seen from FIG. 4, no plasma TNFα concentration could be detected in the 3 groups to which no LPS was administered, but in the group to which LPS was administered but no lactoferrin administered, it was detected in high concentration. In the 2 groups to which lactoferrin was administered, both the bovine-type and human-type lactoferrins significantly inhibited generation of TNFα induced by LPS. In sum, these results indicate that the suppression by lactoferrin of albumin accumulation induced by LPS is based on a different mechanism from the mechanism of the inhibition of TNFα generation in plasma.

Example 3

Study of the Effect of Human-Type Lactoferrin on Alleviation of Symptoms (Accumulation of Ascites and Albumin in the Abdominal Cavity) Resulting from Inflammation Induced by LPS Test Method: The volume of ascites in the abdominal cavity was determined by utilizing the concentration of a certain amount of phenol red solution injected into the abdominal cavity that is diluted depending on the volume of ascites pooled in the cavity.

Six Sprague-Dawley rats of 13 days of age were divided into 3 groups, each consisting of 2 rats. Human-type lactoferrin used in the test was purchased from SIGMA Chemical Co. To all groups was administered 5% casein solution in order to provide uniform proteinous stimulation to the rats. Specifically, to 2 groups involving a control group were intraperitoneally given 100 microliters of 5% casein solution and 100 microliters of phosphate-buffered physiological saline, and to the remaining one group were given 100 microliters of 5% casein solution and 100 microliters of 10% human-type lactoferrin solution. Eighteen hours after the administration, 0.2 microgram/g of body weight of LPS (Difco: B. *E. coli* 055:B5) derived from *Escherichia coli* was intraperitoneally administered. In the control group, an equal amount of phosphate-buffered physiological saline was administered instead of LPS. Five hours after administration of LPS, the infant rats were anesthetized with ether, and 1 ml of chilled phosphate-buffered physiological saline containing 20 microgram of phenol red was intra-peritoneally injected and massaged well to collect lavage-fluid from the abdominal cavity. The lavage-fluid was centrifuged to remove cells of the cavity, and the supernatant (50 microliter) was mixed well with 150 microliters of 0.5M phosphate buffer (pH 7.21) and 50 microliters of distilled water. Thus, coloring of phenol red was measured in absorbance at 559 nm. The same phenol red solution as used in the injection was serially diluted, mixed well with 0.5M phosphate buffer in the same manner as in the sample from the abdominal cavity, and used to obtain a calibration curve. In addition, the albumin concentration in the lavage-fluid of the cavity was determined.

Figure 5:
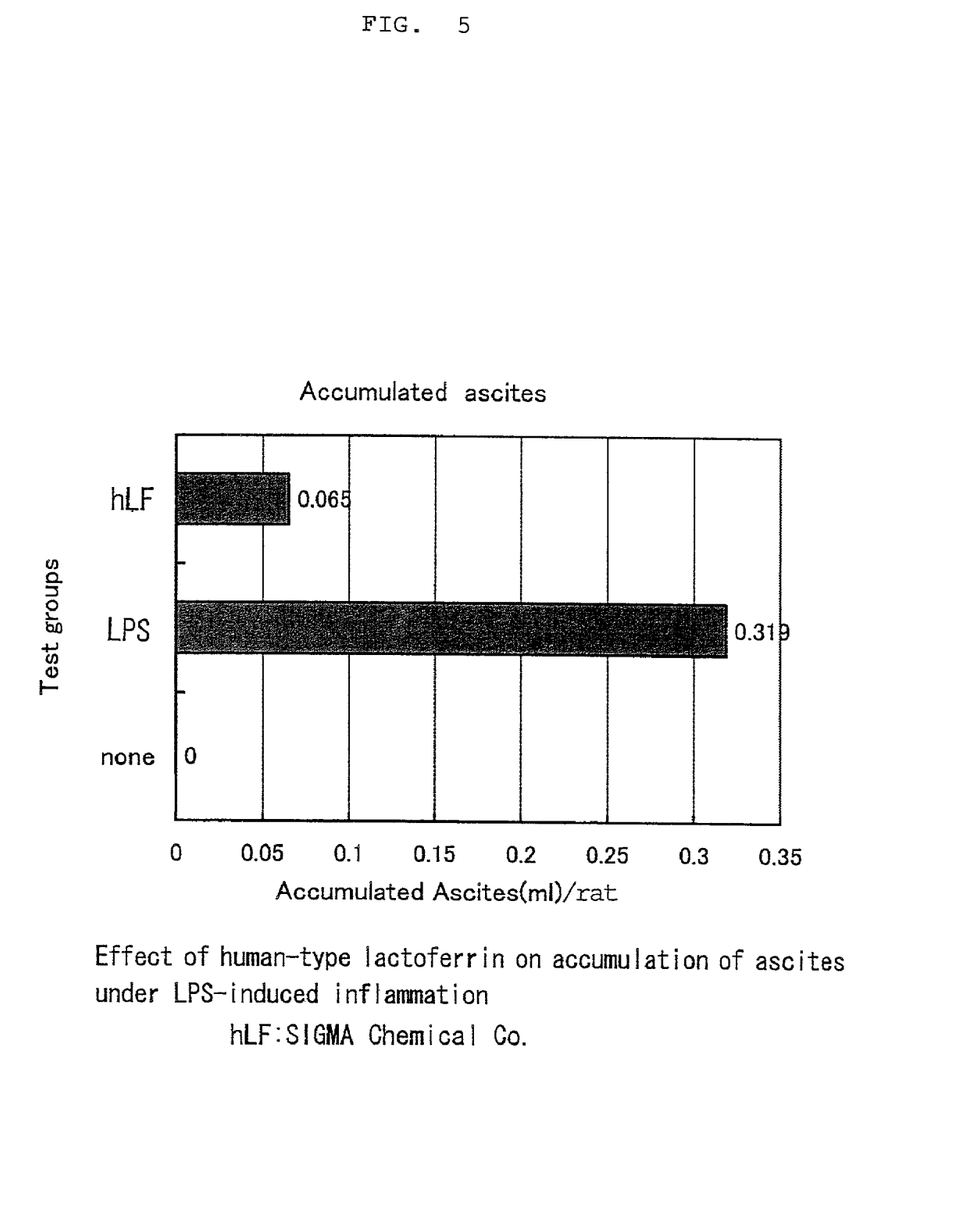
FIG. 5 shows an effect of human-type lactoferrin on decreasing the amount of ascites accumulated in the abdominal cavity 5 hours after administration of LPS.

Test Result: FIG. 5 shows the volume of ascites. In the control group, no ascites that had an influence on the concentration of pigment solution was detected in the abdominal cavity. In the group that was administered with both the lactoferrin and LPS, accumulation of a small amount of ascites was detected, and accumulation of albumin was only 1.6 times as much as that in the control group. On the other hand, in the group to which lactoferrin was not administered but LPS was administered, the volume of accumulated ascites was approximately 5 times as much as that in the lactoferrin-administered group, concentration of the albumin was approximately 2.2 times, and quantity of the albumin was approximately 2.7 times for each rat. And similarly, the albumin concentration in the group in which lactoferrin was not administered but LPS was administered, was 3.6 times as high as that in the control group, and the quantity of the albumin was 4.8 times for each rat. The concentration of accumulated albumin in the abdominal cavity in the rat afforded approximately the same result as that shown in FIG. 1. These results teach as follows. Albumin concentration is relatively decreased as the volume of ascites is increased, and therefore the amount of accumulated ascites is not proportioned directly to the albumin concentration. Accordingly, in a rat in which accumulation of albumin is suppressed, accumulation of ascites might also be suppressed.

Example 4

Study on the Effect of Difference of the Administration Time of Human-Type Lactoferrin on Alleviation of Symptoms (Accumulation of Albumin in the Abdominal Cavity) Resulting from Inflammation Induced by LPS Test Method: In this test method, lactoferrin was administered 18 hours or 15 minutes before or 60 minutes after administration of LPS. Otherwise, the test was carried out in the same manner as in Example 1.

Figure 6:
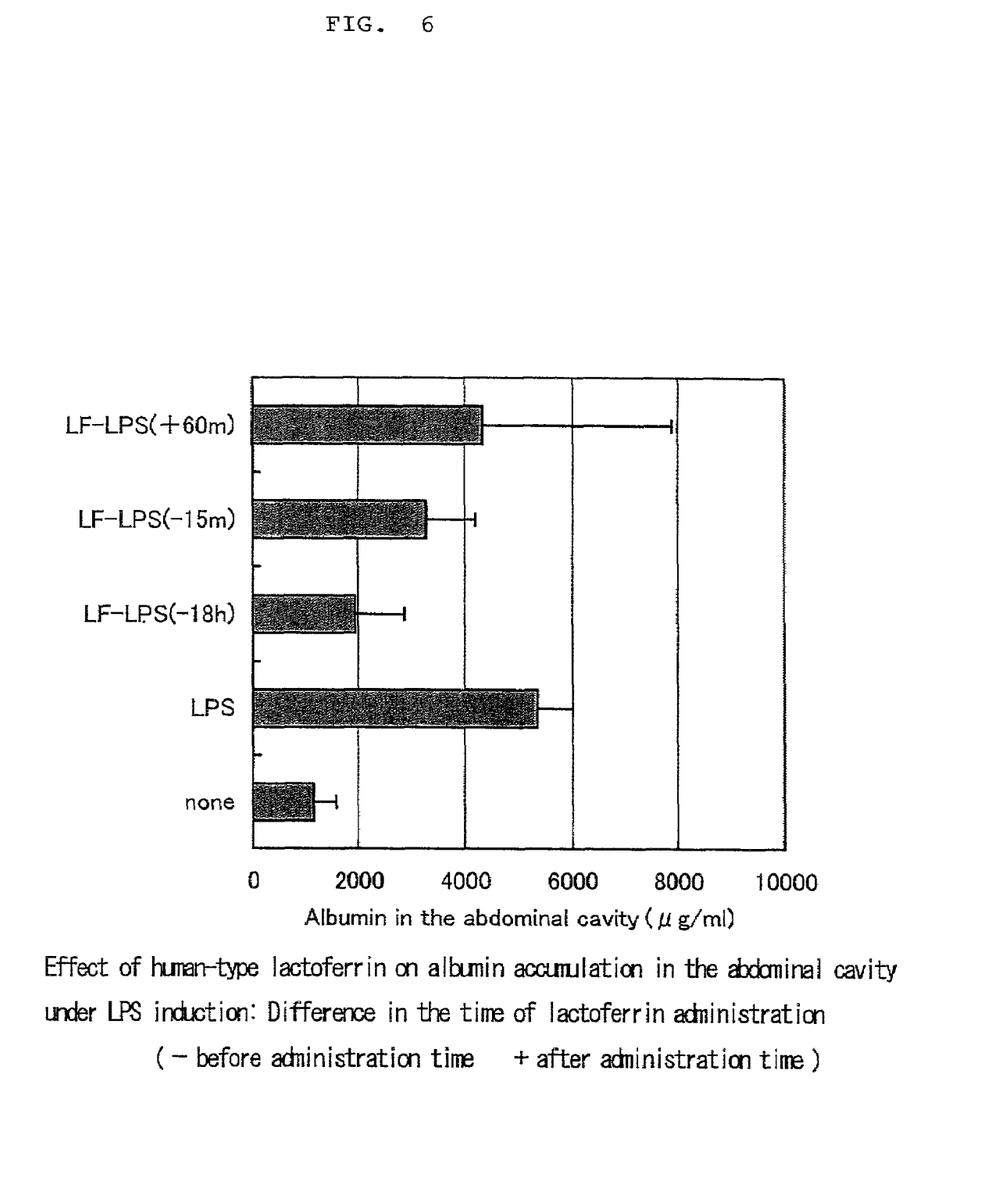
FIG. 6 shows a clear effect of the administration time of lactoferrin on the effect of decreasing accumulation of albumin induced by LPS.

Test Result: As shown in FIG. 6, it was confirmed that the albumin accumulation in the abdominal cavity induced by LPS was significantly suppressed when lactoferrin was administered 18 hours or 15 minutes before administration of LPS, in comparison with the group to which LPS was administered without administration of lactoferrin. When lactoferrin was administered 60 minutes after administration of LPS, the average value decreased though there is no significance. The improving effect of lactoferrin on symptoms resulting from inflammation induced by LPS is highest when lactoferrin is administered preliminarily before administration of LPS, and was found that there is a tendency to decrease the concentration of accumulated albumin even in late administration of lactoferrin.

Example 5

Study on the Effect of Difference of the Administration Route of Human-Type Lactoferrin on Alleviation of Symptoms (Accumulation of Albumin in the Abdominal Cavity) Resulting from Inflammation Induced by LPS The improving effect for symptoms resulting from inflammation induced by LPS was examined by comparing intraperitoneal administration with oral administration of lactoferrin.

Test Method: Sprague-Dawley rats of 11 days of age were divided into 4 groups, each group consisting of 6 rats. These groups comprise a control group, a group to which LPS was administered with no administration of lactoferrin, and similarly in Example 1, a group to which lactoferrin was intraperitoneally administered once 18 hours before administration of LPS, and a group to which lactoferrin was administered intragastrically forcedly by an intragastric probe once a day successively for 3 days until the day before administration of LPS. For the 3 groups other than the intragastrically administered group, a phosphate-buffered physiological saline was administered in the same volume as that of intragastrically administered lactoferrin and in the same manner.

Figure 7:
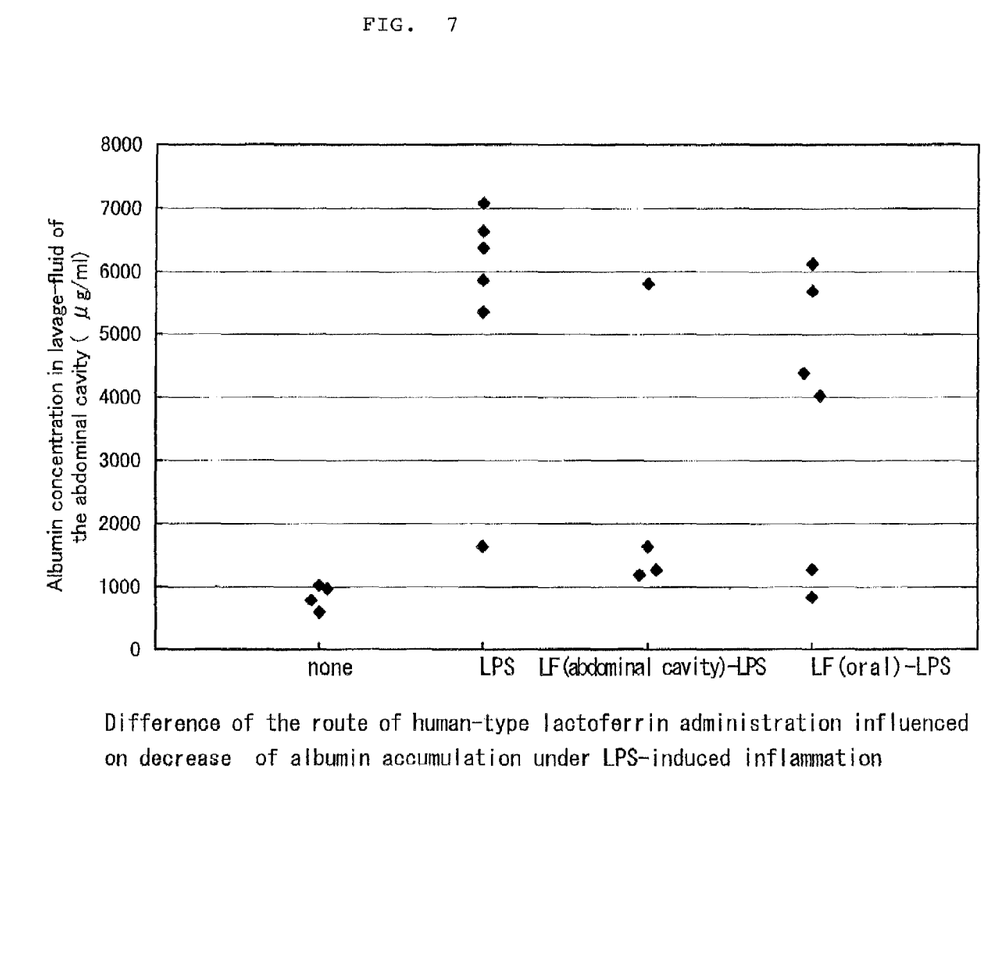
FIG. 7 shows the difference in the administration route of lactoferrin on the effect of decreasing accumulation of albumin induced by LPS in the peritoneal cavity.

Test Result: As seen from FIG. 7, in the group to which LPS was administered but no lactoferrin administered, a large quantity of albumin was accumulated in the abdominal cavity in 5 rats except one. On the other hand, in the group to which lactoferrin was intraperitoneally administered, accumulation of albumin was almost completely inhibited in 3 rats except one, while in the group to which lactoferrin was orally administered into the stomach, accumulation of albumin was observed in 4 of 6 rats. This was applied to a rank-difference test, from which it was found that the level of accumulation was significantly lower than that of the group to which LPS was administered but no lactoferrin was administered. In brief, oral administration of lactoferrin was less effective for alleviation of symptoms induced by LPS than intraperitoneal administration. It was found, however, that successive administration instead of single administration was effective for alleviation of symptoms to some degree.

EFFECTS OF THE INVENTION

The present invention provides novel agents for alleviating symptoms resulting from inflammation, which are effective in alleviating symptoms of inflammation caused by bacterial infection, particularly accumulation of body fluid such as bronchocavemous plasma exudation, ascites, etc., at the inflammatory site, or excessive increase of blood neutrophils.

What is claimed is:

1. A method for reducing a symptom from lipopolysaccharide-induced inflammation resulting from infection by bacteria which produce lipopolysaccharide, comprising administering to a person orally or parenterally, prior to the infection by the bacteria, an effective amount of human-type lactoferrin for a time and under conditions effective to reduce said symptom, wherein said symptom is accumulation of body fluid containing albumin in the abdominal cavity.

2. The method according to claim 1, wherein the effective amount is 1 to 200 mg/kg of body weight/day in intraperitoneal administration.

3. The method of claim 1, wherein the lactoferrin is administered in the form of a tablet.

4. The method of claim 1, wherein the lactoferrin is administered parenterally.

5. The method of claim 1, wherein the lactoferrin is administered intravenously, intramucosally, percutaneously or intraperitoneally.

6. The method according to claim 1, wherein the effective amount is 0.1 to 20 mg/kg of body weight/day in intravenous injection.

7. The method according to claim 6, wherein the effective amount is 0.5 to 10 mg/kg of body weight/day.

8. The method according to claim 1, wherein the effective amount is 5 to 1000 mg/kg of body weight/day in oral administration.

9. The method according to claim 8, wherein the effective amount is 20 to 1000 mg/kg of body weight/day.

10. A method for reducing a symptom from lipopolysaccharide-induced inflammation resulting from infection by bacteria which produce lipopolysaccharide, comprising administering to a person orally or parenterally, prior to the infection by the bacteria, an effective amount of human-type lactoferrin for a time and under conditions effective to reduce said symptom, wherein said symptom is accumulation of albumin at in the abdominal cavity.

11. The method according to claim 10, wherein the effective amount is 1 to 200 mg/kg of body weight/day in intraperitoneal administration.

12. The method of claim 10, wherein the lactoferrin is administered in the form of a tablet.

13. The method of claim 10, wherein the lactoferrin is administered parenterally.

14. The method of claim 10, wherein the lactoferrin is administered intravenously, intramucosally, percutaneously or intraperitoneally.

15. The method according to claim 10, wherein the effective amount is 0.1 to 20 mg/kg of body weight/day in intravenous injection.

16. The method according to claim 15, wherein the effective amount is 0.5 to 10 mg/kg of body weight/day.

17. The method according to claim 10, wherein the effective amount is 5 to 1000 mg/kg of body weight/day in oral administration.

18. The method according to claim 17, wherein the effective amount is 20 to 1000 mg/kg of body weight/day.

* * * * *